(12) United States Patent
Potier et al.

(10) Patent No.: US 7,199,159 B2
(45) Date of Patent: Apr. 3, 2007

(54) USE OF BIGUANIDE DERIVATIVES FOR MAKING A MEDICINE HAVING A WOUND HEALING EFFECT

(75) Inventors: Pierre Jean-Paul Potier, Paris (FR); Nobumichi-André Sasaki, Les Ulis (FR); Maria Conception Achab, Gif sur Yvette (FR); Gisèle Franck, Cachan (FR); Claude Thal, Sceaux (FR); Joanna Bakala, Paris (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 10/297,003

(22) PCT Filed: May 23, 2001

(86) PCT No.: PCT/FR01/01598

§ 371 (c)(1),
(2), (4) Date: Apr. 24, 2003

(87) PCT Pub. No.: WO01/91696

PCT Pub. Date: Dec. 6, 2001

(65) Prior Publication Data

US 2003/0187036 A1 Oct. 2, 2003

(30) Foreign Application Priority Data

May 26, 2000 (FR) .................................. 00 06798

(51) Int. Cl.
*A61K 31/155* (2006.01)
(52) U.S. Cl. .................... 514/635; 514/634; 514/969
(58) Field of Classification Search ................ 514/635, 514/634, 969
See application file for complete search history.

(56) References Cited

U.S. PATENT DOCUMENTS

| | | | |
|---|---|---|---|
| 2,961,377 A | 11/1960 | Shapiro | |
| 3,098,008 A | 7/1963 | Shapiro et al. | |
| 3,174,901 A | 3/1965 | Sterne et al. | |
| 3,468,898 A | 9/1969 | Cutler | |
| 3,808,224 A | 4/1974 | Didier | |
| 3,852,353 A | 12/1974 | Heaphy | |
| 3,929,999 A | 12/1975 | Heaphy | |
| 3,996,232 A | 12/1976 | Diamond et al. | |
| 4,028,402 A | 6/1977 | Fischer et al. | |
| 4,163,800 A * | 8/1979 | Wickett et al. ............. | 514/634 |
| 4,814,334 A * | 3/1989 | Salkin ......................... | 514/256 |
| 4,835,184 A | 5/1989 | Hugelin et al. | |
| 5,567,716 A * | 10/1996 | Della Valle et al. ........ | 514/332 |
| 5,668,084 A | 9/1997 | Unhoch | |
| 5,741,926 A * | 4/1998 | Bierer et al. ................ | 562/457 |
| 5,747,527 A * | 5/1998 | Inman et al. ................ | 514/453 |
| 5,770,582 A | 6/1998 | Bamat et al. | |
| 5,811,078 A * | 9/1998 | Maycock et al. ............ | 424/45 |
| 5,827,898 A * | 10/1998 | Khandwala et al. ........ | 514/734 |
| 5,837,255 A * | 11/1998 | Inman et al. ................ | 514/680 |
| 5,872,145 A * | 2/1999 | Plachetka .................... | 514/415 |
| 6,031,004 A * | 2/2000 | Timmins et al. ............ | 514/635 |
| 6,117,437 A * | 9/2000 | Roreger ....................... | 424/404 |
| 6,228,863 B1* | 5/2001 | Palermo et al. ............. | 514/282 |
| 6,248,363 B1* | 6/2001 | Patel et al. .................. | 424/497 |
| 6,251,428 B1* | 6/2001 | Yoo ............................. | 424/455 |
| 6,414,126 B1* | 7/2002 | Ellsworth et al. ........... | 536/17.2 |
| 6,515,117 B2* | 2/2003 | Ellsworth et al. ........... | 536/17.2 |
| 6,610,746 B2* | 8/2003 | Fryburg et al. ............. | 514/592 |
| 2002/0143039 A1* | 10/2002 | Krajcik et al. .............. | 514/369 |

FOREIGN PATENT DOCUMENTS

| | | |
|---|---|---|
| CN | 1197643 A | 11/1998 |
| EP | 0297828 | 6/1988 |
| EP | 0283369 A2 | 9/1988 |

(Continued)

OTHER PUBLICATIONS

Merck Index(12th edition, 1996), 6001 Metformin, see p. 1014.*

(Continued)

*Primary Examiner*—Vickie Kim
(74) *Attorney, Agent, or Firm*—Blakely Sokoloff Taylor & Zafman

(57) ABSTRACT

The present invention relates to the use of biguanide derivatives of general formula I below:

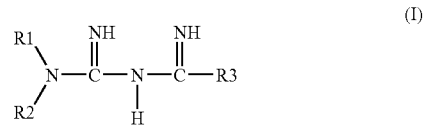

in which:
the groups R1 and R2 represent, independently of each other, a hydrogen atom, a $C_1$–$C_7$, alkyl group, a cycloalkyl group, a heterocycle, a $C_2$–$C_7$ alkenyl group, an aryl group, an aralkyl group, an aryloxyalkyl group or a heteroaryl group, or R1 and R2, taken together, represent a $C_2$–$C_7$ alkylene which may contain one or more hetero atoms, and the group R3 represents a primary, secondary or tertiary amine, or pharmaceutically acceptable salts thereof, to manufacture a medicinal product with cicatrizing action, the said medicinal product being in a pharmaceutical form for topical use.

6 Claims, 3 Drawing Sheets

FOREIGN PATENT DOCUMENTS

| | | | |
|---|---|---|---|
| EP | 0477143 | | 3/1992 |
| EP | 0535446 | A1 | 4/1993 |
| EP | 0535446 | A1 * | 4/1993 |
| EP | 0643044 | B1 | 9/1994 |
| EP | 0852148 | A1 | 7/1998 |
| EP | 0852148 | A1 * | 7/1998 |
| FR | 2.213.778 | | 8/1974 |
| FR | 2320735 | | 3/1977 |
| GB | 852584 | | 5/1957 |
| GB | 21355834 | | 2/1984 |
| JP | 10-265391 | * | 10/1998 |
| JP | 10265391 | | 10/1998 |
| SU | 1560212 | A1 | 4/1990 |
| WO | WO 00/33829 | | 12/1998 |
| WO | WO 01/21159 | A2 | 3/2001 |
| WO | WO2001062237 | * | 8/2001 |

OTHER PUBLICATIONS

U.S. Appl. No. 60/158,773, filed Oct. 23, 1999(Ellsworth et al), pp. 1-82, see especially pp. 37-38(particularly relevant).*

Hyperdictionary(medical), www.hyperdictionary.com, definition of "WOUND" based on 1913 webster dictionary.*

Cicatrization definition form On-line Medical dictionary, Mar. 2000.*

Barletta et al., Action of chlorhexidine gluconated on cicatrization in simple . . . , (abstract only), Revista de al Ascociacion Odontologica Argentina, Oct.-Nov. 1978 vol. 66, Nov. 4, pp. 207-212.*

Nicolaus B.J.R., "Symbiotic Approach to Drug Design", Decision Making in Drug Research, 1983, pp. 173-185.

Diabetes & Metabolism "Membrane Physiology as a Basis For the Cellular Effects of Metformin in Insulin Resistance and Diabetes", Wiensperger N.F., 1999, pp. 110-127.

Diabetic Medicine, "The Influence of Hypoglycaemic Agents on the Growth and Metabolism of Human Endothelial Cells", R. G. Petty et al., 1992, 8 pages.

Weidner, F., Dermatologie"Ummunologic and inflammatory vascular lesions; clinical features and treatment in dermatology; Immunologische und entzundiiche Gefaβschaden: Klinik und therapie in der Dermatologie", THERAPIEWOCHE 29/116 2769-2779 (1979).

Cavaleri, F. et al., Osservazioni sull'impiego degli ipoglicemizzanti orali in dermopazienti diabetici, con particolare riguardo all'associazione glibenclamide-fenformina (Surguan), Terapia Dermatologica, Minerva Dermatologica, 112, pp. 255-266, 1977.

Shornick, J. et al., "Idiopathic atrophie blanche", Journal of the American Academy of Dermatology, 8/6 pp. 792-798, 1983.

Mihailova, Ev et al., "Good healing effects of di-methyl sulphoxide and insulin on necrobiosis liquida diabeticorum in type-1 diabetes", European Journal of Enducinology, vol. 130, n. suppl 2, p. 202, 1992.

Cunliffe, W.J., "Dowling oration 1975. Fibrinolysis and Vasculitis", Clinical and Experimental Dermatology, pp. 1-16, Mar. 1976.

* cited by examiner

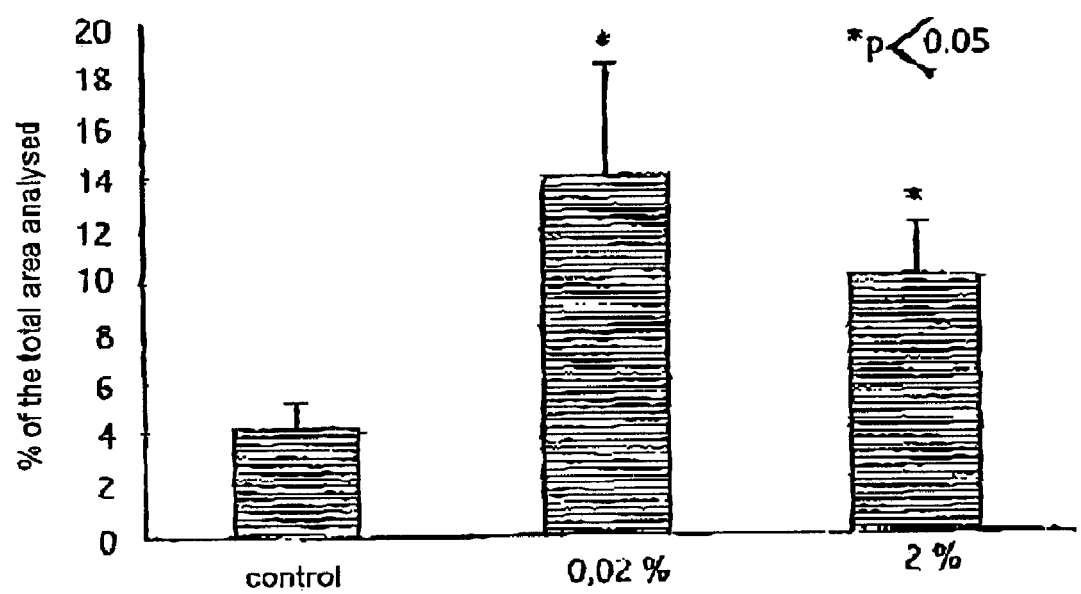
FIG_3

USE OF BIGUANIDE DERIVATIVES FOR MAKING A MEDICINE HAVING A WOUND HEALING EFFECT

The present patent application is a non-provisional application of International Application No. PCT/FR01/01598, filed May 23, 2001.

The present invention relates to the cicatrization of wounds. The invention relates in particular to the use of biguanide derivatives or pharmaceutically acceptable salts thereof, advantageously metformin, to manufacture a medicinal product with cicatrizing action.

The cicatrization of wounds or similar injuries on tissues of various type generally depends on the proliferation of new tissues—epithelial, endothelial and connective. It thus involves a series of co-ordinated cellular and molecular events. It may be delayed or modified by metabolic disturbances which accompany certain long-lasting diseases such as venous insufficiency, arteritis, diabetes and even certain therapies.

The pharmaceutical market currently offers many topical preparations recommended for cicatrizing wounds. In point of fact, their action results from the complementarity of the various products of which they are composed and which give them, to a certain extent, their cicatrizing properly. They protect wounds from the surrounding medium by an antiseptic dressing. They stimulate the development of vascularization and regulate epidormization. These topical forms consist mainly of a lipid mixture (lanolin, petroleum jelly, glycerol, etc.) to which are added acids (salicylic acid, benzoic acid, malic acid), minerals (zinc oxide, titanium oxide) or halides (starch iodide).

Some preparations also contain collagen, fibrinogen, enzymatic serum proteolysate (supply of amino acids) or vitamins (vitamin A) or hormones (4-chloro-testosterone acetate). There is also an ointment (Madecasol® tulgras from the Laboratoires Syntex), the cicatrizating action of which is provided by the addition of a mixture of three triterpenes extracted from the roots of the plant *Centella asiatica* (TCEA). These compounds exert their property by stimulating the biosynthesis of collagen and glycoaminoglycans. However, these extracts may also cause contact allergies in patients.

It is known that one of the complications of diabetes is the appearance of skin complaints such as ulcers (or even ulcerous necrotic angiodermatitis) or perforating dermatoses which the conventional medicinal products used in diabetes treatments do not manage either to control or to treat.

Pharmaceutical compositions based on biguanides are also already known. However, they are only used in the treatment of certain forms of diabetes, and mainly of non-insulin-dependant type II diabetes, as anti-hyperglycaemiant agents which promote the return to glycaemic equilibrium. Metformin is the biguanide derivative most frequently used in this type of treatment.

The daily dosage is between 500 mg and 3 g depending on the diabetic's degree of glycaemia. Metformin has a high therapeutic margin in man and is considered as a medicinal product that is well-tolerated.

The anti-hyperglycaemic effect of metformin is thought to be due firstly to the increase in the endogenous insulin activity and secondly to the action of metformin via insulin-independent mechanisms. Specifically, the action of metformin is reflected by a decrease in the intestinal absorption of glucose, an increase in cellular absorption of blood glucose and a decrease in glucose production by the liver (suppression of neoglucogenesis) and also the amount of insulin required to normalize glycaemia. These effects result partly from the power of metformin to amplify the action of the existing insulin by increasing the activity of the enzyme tyrosine kinase of the insulin receptor, which triggers the "post-receptor" signal cascade.

Patent application FR 2 213 778 discloses novel compositions for treating proliferative skin diseases, which may contain a biguanide derivative: phenformin. Proliferative skin diseases are benign and malignant skin diseases which are characterized by a chronic excessive proliferation of the cells of the epidermis, of the dermis or of their inclusions. The compositions disclosed in this patent application reduce this excessive proliferation and therefore do not have a cicatrizing action, that is to say an acceleration of tissue growth.

Now, the inventors of the present invention have revealed, surprisingly, that biguanide derivatives and in particular metformin also have strong cicatrizing properties, that is to say stimulatory activity towards a complex physiological phenomenon characterized, inter alia, by increased cell growth in the region of the wound. This transient proliferation arises in response to the loss of skin integrity and ensures repair of the deep tissue and reconstitution of the epidermis in the region of the wounds.

Thus, the topical application of this compound in the form of an ointment induces rapid and long-lasting healing of leg ulcers in diabetic individuals and repetition of the topical application of the active principle reinforces this effect. Furthermore, metformin also accelerates the cicatrization of atonic wounds in non-diabetic individuals.

Given the difficulties encountered to control the quality of natural cicatrizing products and the number of laborious steps required to isolate these compounds, biguanide derivatives, whose synthesis is simple, total and rapid, appear to be highly advantageous active principles.

The present invention thus relates to the use of biguanide derivatives of general formula I below:

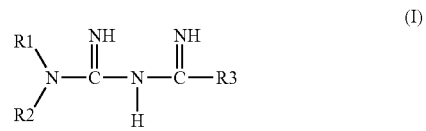

in which:
the groups R1 and R2 represent, independently of each other, a hydrogen atom, a $C_1$–$C_7$ alkyl group, a cycloalkyl group, a heterocycle, a $C_2$–$C_7$ alkenyl group, an aryl group, an aralkyl group, an aryloxyalkyl group or a heteroaryl group, or R1 and R2, taken together, represent a $C_2$–$C_7$ alkylene which may contain one or more hetero atoms, and the group R3 represents a primary, secondary or tertiary amine, or pharmaceutically acceptable salts thereof, to manufacture a medicinal product with cicatrizing action, the said medicinal product being in a pharmaceutical form for topical use. This medicinal product is advantageously intended to be applied to the skin.

For the purposes of the present invention, the expression "$C_1$–$C_7$ alkyl group" means any linear or branched, substituted or unsubstituted $C_1$–$C_7$ alkyl group, such as, for example, methyl, ethyl, propyl, isopropyl or butyl groups and also isomers thereof.

For the purposes of the present invention, the expression "cycloalkyl group" means any cycloalkyl group containing from 3 to 7 carbon atoms, such as, for example, the cyclohexyl group.

For the purposes of the present invention, the term "heterocycle" means any ring containing from 3 to 7 atoms, one or more of which being a hetero atom such as, for example, a nitrogen, oxygen or sulphur atom, the others being carbon atoms.

For the purposes of the present invention, the expression "$C_2$–$C_7$ alkenyl group" means any linear or branched, substituted or unsubstituted $C_2$–$C_7$ alkenyl group, such as vinyl or allyl groups.

For the purposes of the present invention, the expression "aryl group" means any hydrocarbon-based aromatic group such as, for example, the phenyl group, which may contain one or more substituents, such as, for example, a $C_1$–$C_7$ alkyl group as defined above, a $C_2$–$C_7$ alkenyl group as defined above or a halogen.

For the purposes of the present invention, the expression "aralkyl group" means any aryl group as defined above linked via an alkyl as defined above. Advantageously, when the alkyl group represents $CH_2$ and the aryl group represents a phenyl group, this phenyl group is substituted in the manner defined above, and when the alkyl group does not represent $CH_2$, the aryl group is as defined above, advantageously a phenyl group.

For the purposes of the present invention, the expression "aryloxyalkyl group" means any aryl group as defined above linked via an oxyalkyl group whose alkyl residue is as defined above.

For the purposes of the present invention, the expression "heteroaryl group" means any hydrocarbon-based aromatic group containing one or more hetero atoms, such as, for example, sulphur, nitrogen or oxygen atoms, and which can bear one or more substituents, such as, for example, a $C_1$–$C_7$ alkyl group as defined above, a $C_2$–$C_7$ alkenyl group as defined above or a halogen. Examples of heteroaryl groups are furyl, isoxazyl, pyridyl and pyrimidyl groups.

For the purposes of the present invention, the expression "$C_2$–$C_7$ alkylene group" means any $C_2$–$C_7$ alkylene group such as, for example, ethylene, trimethylene, tetramethylene or pentamethylene groups.

For the purposes of the present invention, the expression "pharmaceutically acceptable salt" means any salt prepared from any pharmaceutically acceptable non-toxic acid, including organic acids and mineral acids. Such acids include acetic acid, benzenesulphonic acid, benzoic acid, citric acid, ethanesulphonic acid, fumaric acid, gluconic acid, glutamic acid, hydrobromic acid, hydrochloric acid, lactic acid, maleic acid, malic acid, mandelic acid, methanesulphonic acid, mucic acid, nitric acid, palmoic acid, paintothenic acid, phosphoric acid, succinic acid, tartaric acid and para-toluenesulphonic acid. Hydrochloric acid is advantageously used.

For the purposes of the present invention, the expression "pharmaceutical form for topical use" means any pharmaceutical form intended to be applied to the surface of the wound, in particular to the skin or external or internal mucous membranes, and which acts locally. In particular, the medicinal product may be in a form such as an oil, cream, mousse, liniment, lotion, ointment, liquid, gel, milk, powder or spray. The forms may contain a one-phase vehicle and may consist of a neutral hydroxypropylcellulose gel or a charged gel formed from sodium carboxymethylcellulose. It is also possible to prepare creams, which are forms containing a two-phase vehicle, comprising a hydrophilic phase dispersed in a lipophilic phase. The medicinal product is advantageously in the form of a gel or an ointment. The medicinal product may advantageously be in the form of an active dressing, the said dressing consisting of a support on which the biguanide derivative(s) is (are) impregnated or supported, advantageously in the form of a gel or an ointment. In particular, the active dressing consists of the combination of a hydrocolloid dressing and one or more biguanide derivatives.

In one particular embodiment of the invention, the groups R1 and R2 represent, independently of each other, a hydrogen atom, a $C_1$–$C_7$ alkyl group, a cycloalkyl group, a heterocycle, a $C_2$–$C_7$ alkenyl group, an aryloxyalkyl group or a heteroaryl group.

In another particular embodiment of the invention, the group R3 represents a secondary amine of the following formula:

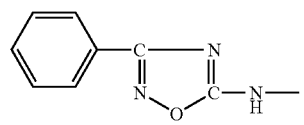

Advantageously, the biguanide derivative used is metformin, even more advantageously in the form of a hydrochloride.

In one particular example, the medicinal product contains from 0.02% to 2% by weight of a biguanide derivative of general formula I or the pharmaceutically acceptable salt thereof and a suitable excipient. These excipients may be chosen from compounds with good compatibility with these active principles. They are, for example, water-soluble polymers of natural polymer type, such as polysaccharides (xanthan gum, carob gum, peptin, etc.) or polypeptides, cellulose derivatives such as methylcellulose, hydroxypropylcellulose or hydroxypropylmethylcellulose, or alternatively synthetic polymers, polaxamers, carbomers, PVA or PVP.

Finally, it is within the competence of a person skilled in the art to add to these medicinal products various excipients, for example co-solvents, for instance ethanol, glycerol or benzyl alcohol, wetting agents (glycerol), agents for facilitating diffusion (transcurol, urea) or antibacterial preserving agents (0.15% methyl p-hydroxybenzoate).

In one particular embodiment of the invention, the biguanide derivatives or pharmaceutically acceptable salts thereof are combined with at least one other active principle. This active principle may be, for example, of the antibiotic, antifungal or antiviral agent type, thus making it possible to accelerate the cicatrization of damaged and infected tissues, simultaneously or in combination with the treatment of the underlying infection.

This active principle may also consist of another agent for improving cicatrization such as, for example, epidermal growth factor, fibroblast growth factor, platelet-derived growth factor, etc.

The biguanide derivatives of general formula I and the pharmaceutically acceptable salts thereof, in particular metformin, advantageously in hydrochloride form, can thus improve the cicatrization of wounds or lesions of any type. These wounds or lesions may be of the type such as surgical incisions, thermal or chemical burns, burns caused by irradiation, abrasions, lacerations, amputations, ischaemic ulcers or bedsores, oral lesions or ulcers or corneal lesions, and in particular those caused by surgery performed on run-down individuals, the elderly, individuals treated by radiotherapy or chemotherapy, or diabetics. This is likewise the case for all dermatoses observed in patients whose cutaneous circulation is deficient (erythemal lesions, vascularitis) and for all wounds observed in diabetic individuals. The pharmaceutical compositions and medicinal products according to the invention also appear to be beneficial in the treatment of tissue necrosis, for example post-thrombotic tissue necrosis.

The examples below of compositions according to the invention are given by way of illustration and with no limiting nature.

EXAMPLES

Several pharmaceutical forms were prepared without preserving agent. The percentages are expressed on a weight basis.

Formulation Example 1

Metformin: 1% by weight relative to the weight of gel.
Neutral gel of hydroxypropylcellulose (Klucel from Aqualon, type 99 MF EP) at 2.9%: remainder to 100%.

Formulation Example 2

Metformin 1% by weight relative to the weight of gel.
Charged gel of sodium carboxymethylcellulose (Aqualon) at 4.5%: remainder to 100%.

Formulation Example 3

Metformin: 1% by weight relative: to the lipophilic phase.
Hydrocorin emulsion (fatty excipient from Roc® containing petroleum jelly, liquid paraffin, triglycerides, polyoxyethylene ethers and ceresin) at 33% (H/L: hydrophilic phase dispersed in a lipophilic phase): remainder to 100%.

This emulsion is prepared at 73° C. by pouring the water in which the metformin has been dissolved into the fatty phase and stirring until cool.

Other subjects and advantages of the invention will become apparent to a person skilled in the art from the detailed description below and by reference to the following illustrative drawings.

FIG. 3 represents the relative surface area occupied by the bundles of collagen in the granulation tissue at D4 according to the percentage of metformin present in the ointment according to Formulation Example 3.

The efficacy of metformin was tested in vivo on skin wounds reproducing ulceration. The pseudo-ulcer was produced on 14-week-old Zucker fa/fa rats by loss of matter of circular shape 8 mm in diameter made by a "punch", down to the muscle layer. The daily treatment of the wound with metformin contained in an ointment according to Formula tion Example 3 at different metformin concentrations systematically led to a significant improvement in cicatrization. The speed of the cicatrization was evaluated by determining the area of the wounds with a video camera coupled to a computer equipped with image analysis software.

Figure 1:
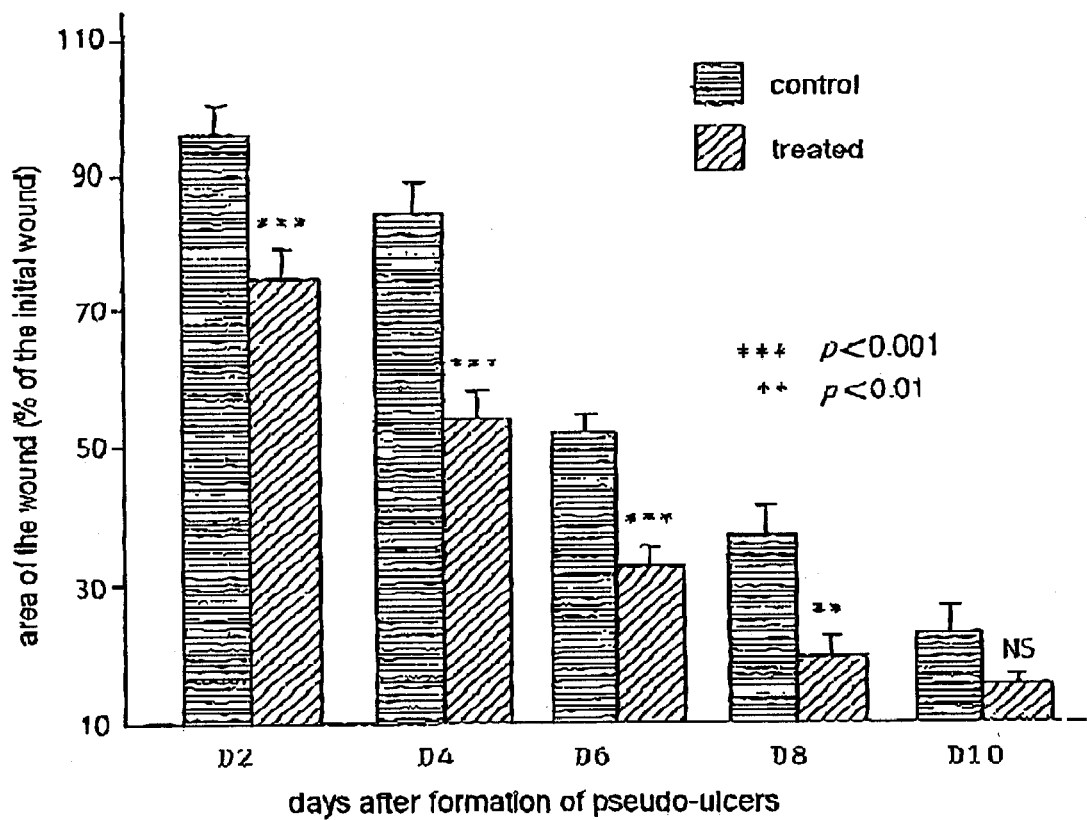
FIG. 1 represents the effect of an ointment according to Formulation Example 3 comprising metformin at 1% by weight relative to the lipophilic phase, on cutaneous cicatrization.

The treatment of the wounds for 10 days (D0–D10) with the ointment according to Formulation Example 3 comprising metformin at a concentration of 1% by weight relative to the lipophilic phase made it possible macroscopically to show a large reduction in the area of the treated wounds relative to the control wounds (FIG. 1). The microscopic evaluation of the cicatrization at D5 and D10 indicates an increase in the quality of the scar tissue in the wounds treated with the ointment according to Formulation Example 3 comprising metformin (more developed granulation tissue, more advanced re-epidermization). Furthermore, metformin at a concentration of 1% by weight relative to the lipophilic phase also appears to exert an effect on neovascularizaton. This effect becomes evident at D5 via a greater density of blood capillaries on the edges of the wound for the treated rats relative to the control rats.

Figure 2:
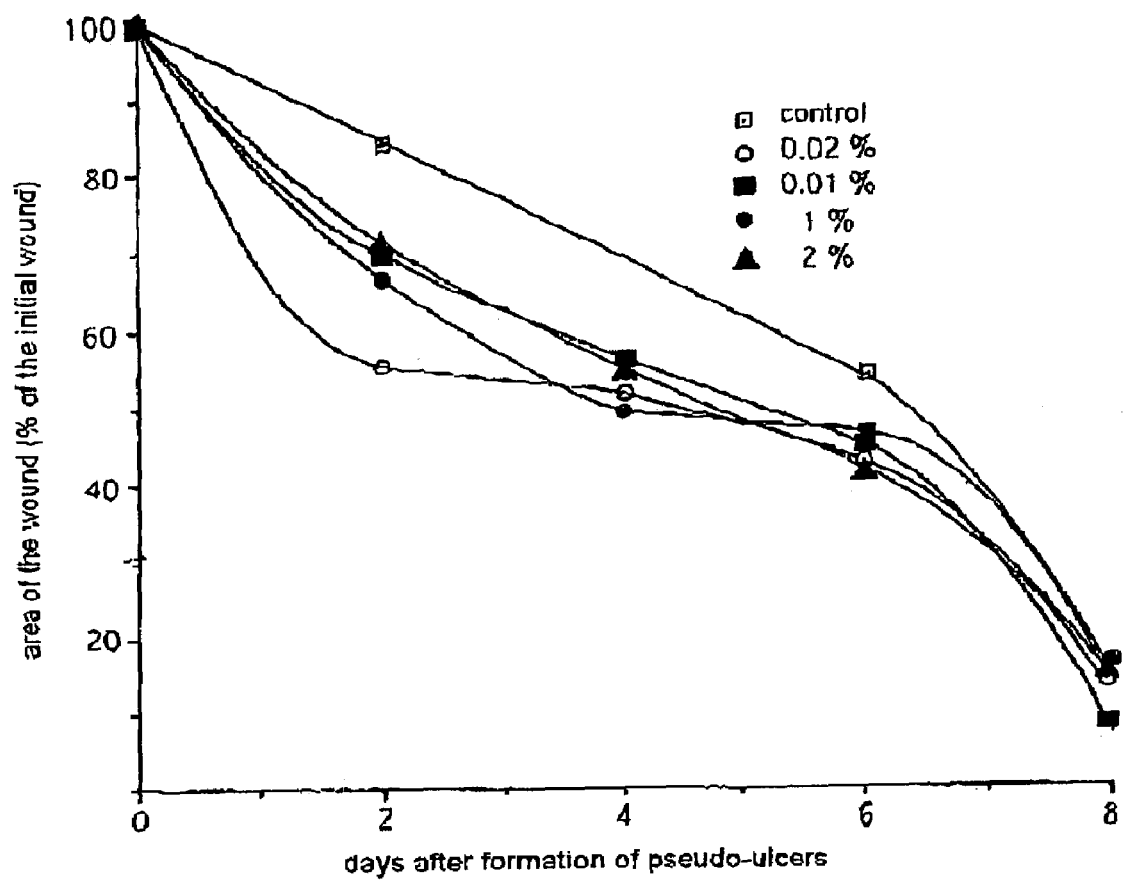
FIG. 2 represents the "dose-response" study of an ointment according to Formulation Example 3 comprising metformin at different concentrations, on cutaneous cicatrization.

The results of a "dose-response" comparative study carried out with an ointment according to Formulation Example 3 comprising metformin at concentrations of 0.02%, 0.1%, and 2% by weight relative to the lipophilic phase reveal cicatrizing action for all the concentrations tested. For the four metformin concentrations used, the closure of the treated wounds is faster than of the untreated control wounds (FIG. 2).

The results of the microscopic analysis of histological sections of the wounds are collated in Table 1 below.

TABLE 1

Effect of different weight concentrations of metformin relative to the lipophilic phase in an ointment according to Formulation Example 3 on the formation of epidermis (biopsy taken from one third of the wound)

| Control | D4 | D6 | D8 | D10 |
|---|---|---|---|---|
| 1 | − | − | ± | + |
| 2 | − | − | + | + |
| 3 | − | − | + | + |
| 4 | − | ± | + | + |
| 5 | − | + | + | + |
| 6 | − | + | + | + |
| Relative average | 0% | 50% | 100% | 100% |

| Ointment comprising 0.02% metformin | D4 | D6 | D8 | D10 |
|---|---|---|---|---|
| 1 | ± | + | + | + |
| 2 | − | + | + | + |
| 3 | + | + | + | + |
| 4 | − | + | + | + |
| Relative average | 50% | 100% | 100% | 100% |

| Ointment comprising 0.1% metformin | D4 | D6 | D8 | D10 |
|---|---|---|---|---|
| 1 | − | + | + | + |
| 2 | − | + | + | + |
| 3 | − | + | + | + |
| 4 | − | + | + | + |
| Relative average | 0% | 100% | 100% | 100% |

| Ointment comprising 1% metformin | D4 | D6 | D8 | D10 |
|---|---|---|---|---|
| 1 | − | + | + | + |
| 2 | − | ± | + | + |
| 3 | + | ± | + | + |
| 4 | − | + | + | + |

TABLE 1-continued

Effect of different weight concentrations of
metformin relative to the lipophilic phase in an ointment
according to Formulation Example 3 on the formation of
epidermis (biopsy taken from one third of the wound)

| Relative average | 25% | 100% | 100% | 100% |
|---|---|---|---|---|
| Ointment comprising 2% metformin | D4 | D6 | D8 | D10 |
| 1 | − | + | + | + |
| 2 | − | − | − | + |
| 3 | − | + | + | + |
| 4 | ± | ± | ± | + |
| Relative average | 25% | 75% | 75% | 100% |

−: absence of epidermis
+: presence of epidermis
±: presence of an epidermis on a portion of the biopsy These results clearly indicate an acceleration of epidermization in animals treated with metformin at the different concentrations compared with untreated control animals.

Moreover, the treatment of wounds with metformin significantly increases the speed of maturation of granulation tissue, which is reflected, inter alia, by an increase in the collagen density (FIG. 3).

The invention claimed is:

1. A method for the cicatrization of wounds comprising administering topically a pharmaceutical composition comprising an effective cicatrizing amount of biguanide derivatives of general formula I below:

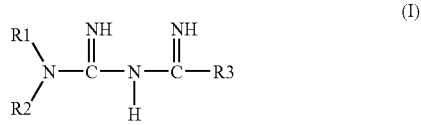

in which:
the groups R1 and R2 represent, independently of each other, a hydrogen atom, a $C_1$–$C_7$ alkyl group, a $C_3$–$C_7$ cycloalkyl group, a phenyl group, a phenyl alkyl group the alkyl group of which is $C_1$–$C_7$,
or R1 and R2, taken together, represent a $C_2$–$C_7$ alkylene which may contain an oxygen atom,
and the group R3 represents a primary amine,
or pharmaceutically acceptable salts thereof, wherein the biguanide derivatives of general formula I is the only cicatrizing agent contained in said pharmaceutical composition.

2. The method according to claim 1 wherein the pharmaceutical composition is in the form of an ointment.

3. The method according to claim 1 wherein the wounds are the wounds of diabetic individuals.

4. The method according to claim 1 wherein the biguanide derivative used is metformin.

5. The method according to claim 2 wherein the ointment is supported or impregnated on a dressing so as to constitute an active dressing.

6. The method according to claim 4 wherein the metformin is in the form of a hydrochloride.

* * * * *